US008563764B2

(12) United States Patent
Choi et al.

(10) Patent No.: US 8,563,764 B2
(45) Date of Patent: Oct. 22, 2013

(54) CATALYST COMPOSITION INCLUDING ZIRCONIUM COMPOUNDS FOR ESTERFICATION REACTION AND METHOD FOR PREPARING ESTER COMPOUNDS

(75) Inventors: Dai-Seung Choi, Daejeon (KR); Sung-Ho Chun, Daejeon (KR); Yu-Chan Kang, Seoul (KR); Heon Kim, Daejeon (KR); Dong-Woo Yoo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 260 days.

(21) Appl. No.: 12/811,797

(22) PCT Filed: Dec. 30, 2008

(86) PCT No.: PCT/KR2008/007801
§ 371 (c)(1),
(2), (4) Date: Jul. 6, 2010

(87) PCT Pub. No.: WO2009/088170
PCT Pub. Date: Jul. 16, 2009

(65) Prior Publication Data
US 2010/0280265 A1    Nov. 4, 2010

(30) Foreign Application Priority Data

Jan. 7, 2008    (KR) ........................ 10-2008-0001789

(51) Int. Cl.
*C07C 69/76*    (2006.01)

(52) U.S. Cl.
USPC ............................................................ 560/8

(58) Field of Classification Search
None
See application file for complete search history.

(56) References Cited

U.S. PATENT DOCUMENTS

| 4,578,165 | A | 3/1986 | Peterson et al. |
| 5,242,877 | A | 9/1993 | Dobson et al. |
| 6,043,335 | A | 3/2000 | Banach et al. |
| 6,372,929 | B1 | 4/2002 | Ridland et al. |
| 2003/0232858 | A1 | 12/2003 | Barker et al. |
| 2004/0015005 | A1 | 1/2004 | Ishihara et al. |
| 2004/0018938 | A1 | 1/2004 | Eng |
| 2005/0113581 | A1 | 5/2005 | Souda et al. |
| 2005/0266139 | A1 | 12/2005 | Lacome et al. |
| 2007/0004936 | A1 | 1/2007 | Ishihara et al. |
| 2007/0010644 | A1 | 1/2007 | Erickson et al. |

FOREIGN PATENT DOCUMENTS

| CN | 1185145 A | 6/1998 |
| CN | 1789303 A | 6/2006 |
| CN | 101054371 A | 1/2007 |
| EP | 1 386 937 A1 | 2/2004 |
| EP | 1 671 991 A2 | 6/2006 |
| EP | 1 674 444 A1 | 6/2006 |
| JP | 871429 | * 3/1996 |
| JP | 08-104665 | 4/1996 |
| JP | 09-221451 | 8/1997 |
| JP | 2001-031748 | 2/2001 |
| JP | 2004-010493 A | 1/2004 |
| KR | 10-0252578 B1 | 4/2000 |
| KR | 10-2003-0042011 A | 5/2003 |
| KR | 10-2005-0050549 A | 5/2005 |
| KR | 10-2006-0065726 A | 6/2006 |
| WO | WO 96/37455 A1 | 11/1996 |
| WO | WO 2006/064685 | 6/2006 |

OTHER PUBLICATIONS

Machine Translation of JP 871429 (1986).*
Database Caplus Chemical Abstracts Service, Columbus, Ohio, US; Database Accession No. 1996:367446, Abstract of Takahara et al. "Esterification catalysts and preparation of esters"; JP 08071429. See also Tabl1 of the attached Machine Translation of JP 429.*
Mebah et al.: "Synthesis of Sufurated Acrylic Compounds by Esterification and Transesterification", Sulfur Letters, vol. 17, No. 5, Dec. 31, 1994, pp. 251-256, XP002641949.
Nakayama Masaya et al.: "Water-Tolerant and Reusable Catalysts for Direct Ester Condensation between Equimolar Amounts of Carboxylic Acids and Alcohols", Advanced Synthesis & Catalysis, WileyVCH Verlag, Weinheim, DE, vol. 346, No. 11, Jan. 1, 2004, pp. 1275-1279, XP002440774.
Database WPI week 200825 Thomson Scientific, London, GB; AN 2008-D29054, XP002641948.
Kumar et al., "Catalytic Role of Diorganotin Dichloride in Esterification of Carboxylic Acids", Tetrahedron Letters, vol. 28, No. 32, pp. 3713-3714, 1987.
Nitta et al., "Photochemical Cycloaddition of Benzophenone with 1,5-Dimethyl-6-Methylenetricyclo[$3.2.1.0^{2,7}$]Oct-3-En-8-One and a Related Alcohol; A Striking Substituent Effect on the Product Composition", Chemistry Letters, pp. 55-58, 1977.
Izumi et al., "Catalysis of Heteropoly Acids Entrapped in Activated Carbon", Chemistry Letters, pp. 663-666, 1981.
Otera et al., "Novel Template Effects of Distannoxane Catalysts in Highly Efficient Transesterification and Esterification", J. Org. Chem., vol. 56, pp. 5307-5311, 1991.
Toda et al., "Biodiesel made with sugar catalyst", Nature, vol. 438, pp. 178, 2005.
Olah et al., "Synthetic Methods and Reactions; 51[1]. A convenient and Improved Method for Esterification over Nafion-$H^2$, a Superacidic Perfluorinated Resinsulfonic Acid Catalyst", Synthesis, pp. 929-930, 1978.

* cited by examiner

Primary Examiner — Karl J Puttlitz
(74) Attorney, Agent, or Firm — McKenna, Long & Aldridge, LLP

(57) ABSTRACT

The present invention relates to an esterification catalyst composition that includes a zirconium compound and a method for producing an ester compound, which includes the steps of esterifying alcohol and carboxylic acid compounds by using the same, and it may be applied to a mass synthesis process.

3 Claims, No Drawings

CATALYST COMPOSITION INCLUDING ZIRCONIUM COMPOUNDS FOR ESTERFICATION REACTION AND METHOD FOR PREPARING ESTER COMPOUNDS

TECHNICAL FIELD

The present invention relates to an esterification catalyst composition that includes a zirconium compound and a method for producing an ester compound by using the same.

This application is a 35 U.S.C. §371 National Stage entry of International Application No. PCT/KR2008/007801, filed on Dec. 30, 2008, and claims priority to Korean Application No. 10-2008-0001789, filed on Jan. 7, 2008, which are all hereby incorporated by reference in their entireties.

BACKGROUND ART

An esterification reaction that is one of representative reactions of organic synthesis is an important reaction that has high utility value in views of environmentally friendly chemical processes, and many studies thereof have been reported.

For example, in order to synthesize biodiesel having high quality from vegetable-oil including an oleic acid and a stearic acid, an esterification reaction is applied using a catalyst, an importance of which has been embossed (Nature 438, 178, 2005).

In general, the esterification reaction frequently uses a coupling agent and an auxiliary activator in an amount of 1 equivalent or more on the basis of reactants, and after the reaction, since a great amount of side products are generated, an additional purification process such as distillation or recrystallization is required.

In addition, in a real reaction, if any one of a carboxylic acid and alcohol is not used in an excessive amount, there is a problem in that it is impossible to obtain efficiently ester (for example, see Synthesis, 1978 p. 929, Chem. Lett, 1977 p. 55, Chem. Lett. 1981 p. 663, Tetrahedron. Lett. 28, 1987 p. 3713, J. Org. Chem. 56, 1991 p. 5307). However, as described above, it is ideal to directly perform esterification from the carboxylic acid and alcohol in the same or similar mole number while the reactant is used in an excessive amount.

Accordingly, currently, by using the carboxylic acid and alcohol in almost the same mole number, a catalyst for synthesizing ester has been developed.

For example, Korean Patent Application Laid-Open No. 2003-0042011 relates to a method for producing an ester condensate, and a synthesis reaction of a monomer ester or thioester, or polyester or polythioester by using a tetravalent hafnium compound represented by hafnium chloride (IV), particularly, hafnium chloride (IV) (THF)$_2$ or hafnium (IV)t-butoxide as a (poly)condensation catalyst.

In addition, Korean Patent Application No. 2006-0065726 (Registration No.: 0729714) discloses an example of esterification reaction by using a catalyst that includes zirconium (IV) compound and/or hafnium(IV) compound and iron compound and/or gallium compound. At this time, as the zirconium(IV) compound, a compound that is represented by Zr(OH)$_a$(OR1)$_b$ (R1 is an acyl group or an alkyl group, a and b are each an integer in the range of 0 or 1~4, and a+b=4), or zirconium(IV) halogenate is used.

However, even though the hafnium compound, the zirconium halogenate, and the zirconium compound have excellent performance, there is a disadvantage in that it is not well dissolved in a nonpolar solvent such as heptane, octane, and toluene at normal temperature because of a characteristic of inorganic salt compound. In addition, after the reaction is finished, while the post-treatment is performed, catalyst residuals remain on a wall of a reactor. Thus, there is a problem in that it is difficult to remove the residuals. In the case of when synthesis is performed by using a great amount of reactant in a factory, there is a problem in that a process for washing a vessel is further required, and after the reaction is performed, many problems, for example, an additional removal of catalyst residuals that are not dissolved in a final solution, are included.

In addition, Korean Patent Application Laid-Open No. 2005-0050549 discloses an example of production of carboxylic acid ester by reacting a carboxylic acid and a monohydroxy compound in the presence of a catalyst after the zirconium catalyst is produced by reacting the monohydroxy compound and a Zr(OR)$_4$ type of (R is an alkyl group or an aryl group) zirconium compound with each other. At this time, a ligand that is bonded to a zirconium element is a form where an oxygen atom is included in one single molecule (monodentate).

DISCLOSURE

Technical Problem

Accordingly, in order to solve the above problems, it is an object of the present invention to provide an esterification catalyst composition including a zirconium compound, which has high solubility to a nonpolar solvent, is capable of producing an ester compound at high yield, and is applied to a mass synthesis process, and a method for producing an ester compound using the same.

Technical Solution

The present invention provides an esterification catalyst composition which comprises a compound that is represented by the following Formula 1:

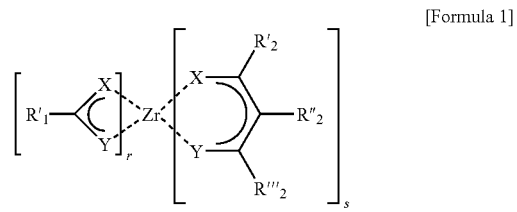

[Formula 1]

wherein

X and Y are each independently a hetero atom that is S or O;

$R_1'$, $R_2'$, $R_2''$ and $R_2'''$ are each independently any one selected from the group consisting of hydrogen; halogen; straight- or branched-chained alkyl that is unsubstituted or substituted with halogen or hydrocarbons and has 1 to 20 carbon atoms; straight- or branched-chained alkenyl that is unsubstituted or substituted with hydrocarbons and has 1 to 20 carbon atoms; cycloalkyl that is unsubstituted or substituted with hydrocarbons and has 3 to 12 carbon atoms; aryl that is unsubstituted or substituted with hydrocarbons and has 6 to 40 carbon atoms; aralkyl that is unsubstituted or substituted with hydrocarbons and has 7 to 15 carbon atoms; alkynyl having 2 to 20 carbon atoms; alkynyl having 2 to 20 carbon atoms; straight- or branched-chained alkoxy that is unsubstituted or substituted with halogen, vinyl or hydrocarbons and has 1 to 20 carbon atoms; straight- or branched-chained carbonyloxy that is unsubstituted or substituted with halogen, or hydrocarbons and has 1 to 20 carbon atoms, r and s are each independently an integer in the range of 0 to 4, and r+s=4, and the hydrocarbons may be selected from the group consisting of an alkyl group including a methyl group, an ethyl group, a propyl group, an isopropyl group, a butyl group, a tertiary-butyl group, a pentyl group, a hexyl group, and a heptyl group; a cycloalkyl group including a cyclopentyl group and a cyclohexyl group; and an aryl group including a phenyl group, a naphthyl group, an anthracenyl group, a biphenyl group, a pyrenyl group, and a perylenyl group.

In addition, the present invention provides a method for producing an ester compound, which comprises the steps of esterifying alcohol and carboxylic acid compounds by using the esterification catalyst composition.

Advantageous Effects

An esterification catalyst composition according to the present invention has high solubility to a nonpolar solvent and is capable of producing an ester compound at high yield, thus a method for producing an ester sulfur compound using the same is very easily applied to a mass production process.

Best Mode

Hereinafter, the present invention will be described in detail.

A zirconium compound that is used in the present invention and is represented by Formula 1 is a form in which a bidentate ligand where two or more oxygen atoms or sulfur atoms are included in a single molecule is directly coordinated with a zirconium element. Since this form includes a plurality of ligands having organic functional groups as compared to a catalyst including salts, solubility to a nonpolar solvent such as toluene, heptane and the like is excellent. Thus, after the esterification reaction is carried out, the catalyst residuals do not remain. Accordingly, it is useful to posttreatment and very easily applied to a mass production process.

The compound that is represented by Formula 1 may include a compound that is represented by the following Formula 2:

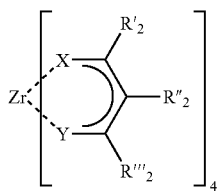

[Formula 2]

wherein X, Y, $R_2'$, $R_2''$ and $R_2'''$ are as defined in Formula 1.

For example, the compound that is represented by Formula 1 may include zirconium acetylacetonate [Zr(acac)$_4$], tetrakis (2,2,6,6-tetramethyl-3,5-heptanedionato)zirconium [Zr (TMHD)$_4$], zirconium hexafluoroacetylacetonate [Zr (CF$_3$COCHCOCF$_3$)$_4$] and zirconium trifluoroacetylaceton [Zr(CF$_3$COCHCOCH$_3$)$_4$].

The esterification catalyst composition according to the present invention may be used while being carried in a solid phase or a particulate support phase. At this time, it is preferable that the particulate support is one or more selected from the group consisting of silica, titania, silica/cromia, silica/cromia/titania, silica/alumina, aluminium phosphate gel, silanated silica, silica hydro gel, montmorilonite clay and zeolite.

A method for producing an ester compound according to the present invention comprises the steps of esterifying alcohol and carboxylic acid compounds by using the esterification catalyst composition to produce the ester compound.

The alcohol that is used in the method for producing an ester compound according to the present invention may include compounds that are represented by the following Formulas 3 to 8:

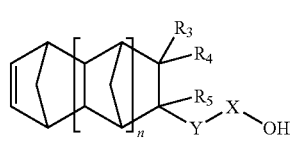

[Formula 3]

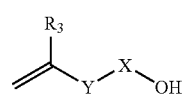

[Formula 4]

In Formulas 3 and 4, n is an integer in the range of 0 to 4,

Y is a direct bond; or a polar functional group selected from the group consisting of —C(O)—O—, —O—C(O)—, —C(O)N(R$_3$)—, —OC(O)N(R$_3$)—, —N(R$_3$)—, —C(O)—, —SO$_2$—, —SO$_3$— and —OSO$_2$—, X is a direct bond; or any one selected from the group consisting of —(OCH$_2$)$_m$- (m is an integer in the range of 0 to 10); substituted or unsubstituted alkylene having 1 to 20 carbon atoms; substituted or unsubstituted alkenylene having 2 to 20 carbon atoms; substituted or unsubstituted cycloalkylene having 3 to 12 carbon atoms; substituted or unsubstituted arylene having 6 to 40 carbon atoms; substituted or unsubstituted aralkylene having 7 to 15 carbon atoms; and substituted or unsubstituted alkynylene having 2 to 20 carbon atoms;

R$_3$, R$_4$ and R$_5$ are each independently any one selected from the group consisting of hydrogen; halogen; straight- or branched-chained alkyl having 1 to 20 carbon atoms; straight- or branched-chained vinyl or alkenyl having 2 to 20 carbon atoms; alkynyl having 2 to 20 carbon atoms; cycloalkyl that is unsubstituted or substituted with hydrocarbons and has 3 to 12 carbon atoms; aryl that is unsubstituted or substituted with hydrocarbons and has 6 to 40 carbon atoms; and aralkyl that is unsubstituted or substituted with hydrocarbons and has 7 to 15 carbon atoms,

[Formula 5]

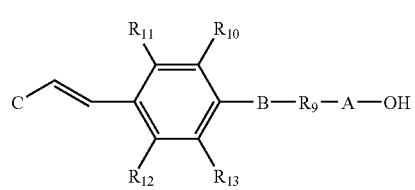

[Formula 6]

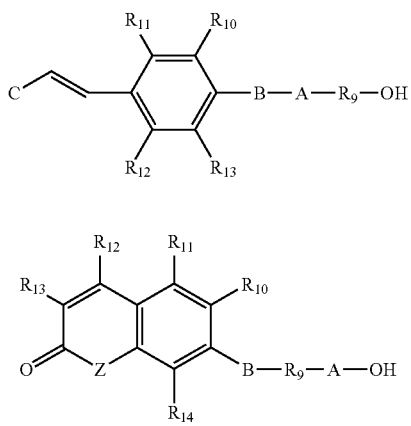

[Formula 7]

[Formula 8]

in the compounds that are represented by Formulas 5 to 8,

A is a direct bond; or any one selected from the group consisting of substituted or unsubstituted alkylene having 1 to 20 carbon atoms; carbonyl [—C(O)—]; carboxy [—C(O)O— or —OC(O)—]; and substituted or unsubstituted arylene having 6 to 40 carbon atoms, B is a direct bond; oxygen, sulfur or —NH—, Z is oxygen or sulfur, $R_9$ is a direct bond; or any one selected from the group consisting of substituted or unsubstituted alkylene having 1 to 20 carbon atoms; substituted or unsubstituted alkenylene having 2 to 20 carbon atoms; substituted or unsubstituted cycloalkylene having 3 to 12 carbon atoms; substituted or unsubstituted arylene having 6 to 40 carbon atoms; substituted or unsubstituted aralkylene having 7 to 15 carbon atoms; and substituted or unsubstituted alkynylene having 2 to 20 carbon atoms, $R_{10}$, $R_{11}$, $R_{12}$, $R_{13}$ and $R_{14}$ are each independently any one selected from the group consisting of substituted or unsubstituted alkyl having 1 to 20 carbon atoms; substituted or unsubstituted alkoxy having 1 to 20 carbon atoms; substituted or unsubstituted aryloxy having 6 to 30 carbon atoms; and substituted or unsubstituted aryl having 6 to 40 carbon atoms, and C is a compound that includes hetero aryl including Groups 14, 15, or 16 hetero atoms, for example, S, O, N and the like, and having 6 to 40 carbon atoms; or aryl having 6 to 40 carbon atoms. In detail, C may be represented by the following Formulas:

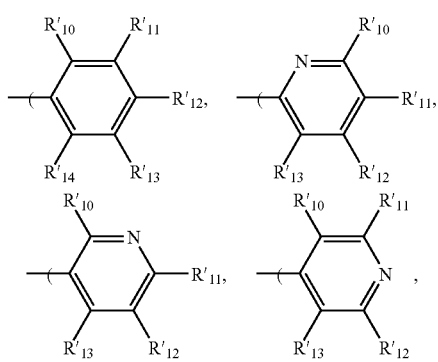

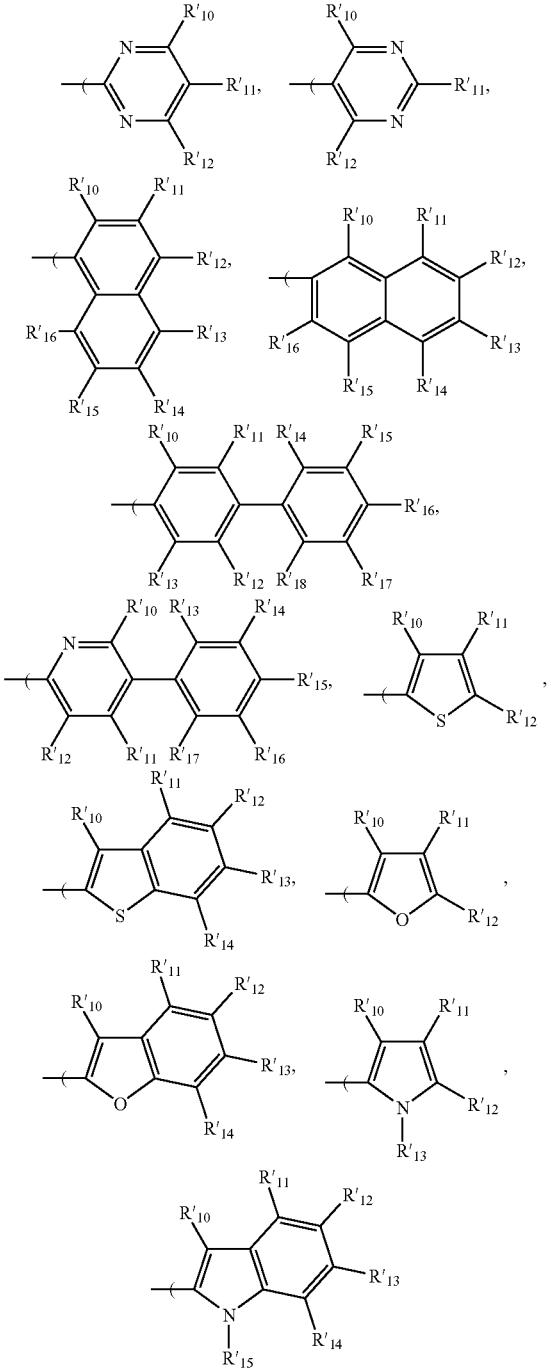

wherein $R'_{10}$, $R'_{11}$, $R'_{12}$, $R'_{13}$, $R'_{14}$, $R'_{15}$, $R'_{16}$, $R'_{17}$ and $R'_{18}$ are each independently hydrogen; halogen; or any one selected from the group consisting of substituted or unsubstituted alkyl having 1 to 20 carbon atoms; substituted or unsubstituted alkoxy having 1 to 20 carbon atoms; substituted or unsubstituted aryloxy having 6 to 30 carbon atoms; and substituted or unsubstituted aryl having 6 to 40 carbon atoms, and ─( is a connection portion.

The hydrocarbons may be selected from the group consisting of an alkyl group including a methyl group, an ethyl group, a propyl group, an isopropyl group, a butyl group, a tertiary-butyl group, a pentyl group, a hexyl group, and a heptyl group; a cycloalkyl group including a cyclopentyl group and a cyclohexyl group; and an aryl group including a phenyl group, a naphthyl group, an anthracenyl group, a biphenyl group, a pyrenyl group, and a perylenyl group, and in the case of when substituted or unsubstituted alkylene, alkenylene, cyclo alkylene, arylene, aralkylene, and alkynylene are substituted, they may be substituted with the above hydrocarbons.

As the alcohol, alcohol that includes primary alcohol, secondary alcohol, tertiary alcohol and the like, and has straight-chained or cyclic substituent groups such as alkyl group, alkenyl group, aryl group and the like may be used.

For example, examples of the alcohol may include aliphatic primary alcohols including methanol, ethanol, n-propanol, n-butanol, n-hexanol, n-heptanol, n-octanol, n-decanol, n-dodecanol, stearyl alcohol, 2-ethylhexane-1-ol and neopentyl alcohol; aromatic primary alcohols of benzyl alcohol; aliphatic secondary alcohols including isopropyl alcohol, s-butyl alcohol and 1-methylhexane-1-ol; alicyclic secondary alcohols including cyclohexanol and 2-adamanthirol; tertiary alcohols including t-butyl alcohol, 1-adamanthirol, phenol, o-cresol, m-cresol, p-cresol, 3,5-dimethylphenol, α-naphthol and β-naphthol; and polyvalent alcohols including ethylene glycol, propylene glycol, trimethylene glycol, 1,4-butanediol, 1,5-pentanediol, 1,6-hexanediol, 1,7-heptanediol, 1,8-octanediol, pinacol, neopentyl glycol, trimethylol propane, trimethylol ethane, pentaerythritol, dipentaerythritol, sorbitol and polyvinyl alcohol.

The alcohol may be used alone or as a mixture of two or more species. For example, in polyvalent alcohol that has a primary hydroxy group and a secondary hydroxy group, a condensation reaction of a carboxylic acid having a large volume and a primary hydroxy group may be selectively generated, or as a distance between the primary hydroxy group and the secondary hydroxy group is increased, a condensation reaction with the primary hydroxy group may be selectively generated, thus an ester condensate may be chemically selectively generated.

The carboxylic acid that is used in the production method of the ester compound according to the present invention may include compounds that are represented by the following Formulas 9 to 14.

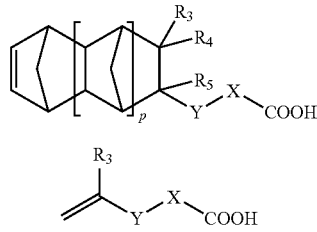

[Formula 9]

[Formula 10]

In Formulas 9 and 10, p is an integer in the range of 0 to 4,

Y is a direct bond; or a polar functional group selected from the group consisting of —C(O)—O—, —O—C(O)—, —C(O)N($R_3$)—, —OC(O)N($R_3$)—, —C(O)—, —$SO_2$—, —$SO_3$— and —$OSO_2$—, X is a direct bond; or any one selected from the group consisting of —(OCH$_2$)$_q$-(q is an integer in the range of 0 to 10); substituted or unsubstituted alkylene having 1 to 20 carbon atoms; substituted or unsubstituted alkenylene having 2 to 20 carbon atoms; substituted or unsubstituted cycloalkylene having 3 to 12 carbon atoms; substituted or unsubstituted arylene having 6 to 40 carbon atoms; substituted or unsubstituted aralkylene having 7 to 15 carbon atoms; and substituted or unsubstituted alkynylene having 2 to 20 carbon atoms;

$R_3$, $R_4$ and $R_5$ are each independently any one selected from the group consisting of hydrogen; halogen; straight- or branched-chained alkyl having 1 to 20 carbon atoms; straight- or branched-chained vinyl or alkenyl having 2 to 20 carbon atoms; cycloalkyl that is unsubstituted or substituted with hydrocarbons and has 3 to 12 carbon atoms; aryl that is unsubstituted or substituted with hydrocarbons and has 6 to 40 carbon atoms; aralkyl that is unsubstituted or substituted with hydrocarbons and has 7 to 15 carbon atoms; and alkynyl having 2 to 20 carbon atoms,

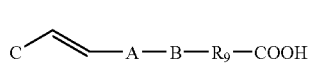

[Formula 11]

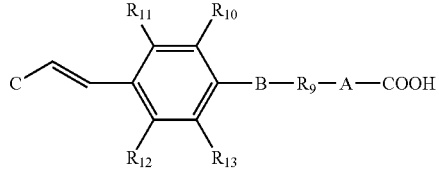

[Formula 12]

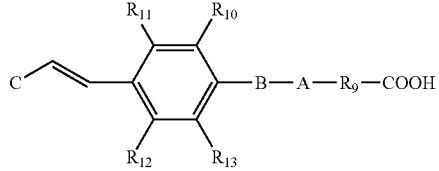

[Formula 13]

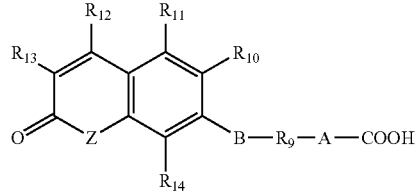

[Formula 14]

In Formulas 11 to 14, A, B, C, Z, $R_9$ and $R_{10}$, $R_{11}$, $R_{12}$, $R_{13}$ and $R_{14}$ are as defined in Formulas 5 to 8.

The hydrocarbons may be selected from the group consisting of an alkyl group including a methyl group, an ethyl group, a propyl group, an isopropyl group, a butyl group, a tertiary-butyl group, a pentyl group, a hexyl group, and a heptyl group; a cycloalkyl group including a cyclopentyl group and a cyclohexyl group; and an aryl group including a phenyl group, a naphthyl group, an anthracenyl group, a biphenyl group, a pyrenyl group, and a perylenyl group, and in the case of when substituted or unsubstituted alkylene, alkenylene, cyclo alkylene, arylene, aralkylene, and alkynylene are substituted, they may be substituted with the above hydrocarbons.

It is preferable that the carboxylic acid used in the esterification reaction is chain type or cyclic type of fatty acids or aromatic acids as monocarboxylic acids or acids having unsaturated bonds or substituent groups to them.

For example, the carboxylic acid compound may include fatty acids including acetic acid, a propionic acid, a n-butyric acid, an isobutyric acid, a n-valeric acid, an isovaleric acid, methylethyl acetic acid, trimethyl acetic acid, a caproic acid, an enantic acid, a caprylic acid, a pelargonic acid, a capric acid, an undercylic acid, a lauric acid, a tridecylic acid, a myricstic acid, a pentadecylic acid, a palmitic acid, a heptadecylic acid, a stearic acid, an acrylic acid, a crotonic acid, an isocrotonic acid, a undecylenic acid, an oleic acid, an elaidic acid, an erucic acid, a brassidic acid, a sorbic acid, a linoleic acid and a linolenic acid; aromatic acids such as benzoic acid; dicarboxylic acids such as a malonic acid, a succinic acid, a glutaric acid, an adipic acid, a pimelic acid, a suberic acid, an azelaic acid, a sebacic acid, a dodecanedioic acid, a fumaric acid, a maleic acid, a mesaconic acid, a citraconic acid, a phthalic acid, a terephthalic acid, an isophthalic acid and a diphenyl ether-4,4'-dicarboxylic acid; tricarboxylic acids including a butane-1,2,4-tricarboxylic acid, a cyclohexane-1,2,3-tricarboxylic acid, a benzene-1,2,4-tricarboxylic acid and a naphthalene-1,2,4-tricarboxylic acid; and tetracarboxylic acids including a butane-1,2,3,4-tetracarboxylic acid, a cyclobutane-1,2,3,4-tetracarboxylic acid, a benzene-1,2,4,5-tetracarboxylic acid, a 3,3',4,4'-benzophenone tetracarboxylic acid and a 3,3',4,4'-diphenylether tetracarboxylic acid.

In the method for producing an ester compound according to the present invention, it is preferable that the carboxylic acid and alcohol are used in the same mole number. In detail, if the monovalent carboxylic acid and alcohol are used, an ester monomer is obtained, and if polyvalent carboxylic acid such as α,ω-aliphatic dicarboxylic acids and polyvalent alcohol such as α,ω-aliphatic diol are used, polyester may be synthesized.

The production method of the ester compound according to the present invention is preferable in that by using the esterification catalyst composition according to the present invention, the alcohol compound and the carboxylic acid compound are reacted with each other in the same mole number to efficiently produce the ester compound. In addition, it is preferable that the esterification catalyst composition is added at a ratio of 0.01 to 20 on the basis of a mole number of the compound that is added in a smaller amount among the alcohol or carboxylic acid compounds in the reaction solution. If the amount of the esterification catalyst composition is less than 0.01 mole, there is a problem in that the yield is reduced. If the amount is more than 20 mole, there is a problem in that since reaction byproducts are increased, the purity is reduced.

In addition, as the alcohol and carboxylic acid that are used in the production method of the ester compound according to the present invention, a ω-hydroxycarboxylic acid that each has independently a hydroxyl group and a carboxy group at both ends in one molecule may be used.

For example, the ω-hydroxycarboxylic acid includes ω-hydroxy undecanoic acid, hydroxy dodecanoic acid, p-hydroxy benzoic acid, m-hydroxy benzoic acid, 6-hydroxynaphthalene-2-carboxylic acid, 4-(p-hydroxyphenoxy)benzoic acid, 3-(p-hydroxyphenoxy)benzoic acid, 4-(m-hydroxyphenoxy)benzoic acid and 3-(m-hydroxyphenoxy) benzoic acid.

The solvent that is used in the production method of the ester compound according to the present invention is not particularly limited, and a polar solvent, a nonpolar solvent or a mixed solvent thereof may be used. The nonpolar solvent is preferable because of easiness of removal of the products by the esterification reaction to the outside of the reaction system. The organic solvent used while the catalyst composition according to the present invention is dissolved therein is preferable because it forms an azeotropic point in conjunction with water.

It is preferable that the total weight of the organic solvent in the above reaction system is in the range of 0.1 to 100 on the basis of a weight of the compound that is added in a smaller amount among the alcohol or carboxylic acid compounds, and it is more preferable that the total weight is in the range of 0.5 to 50.

It is preferable that the nonpolar solvent is selected from the group consisting of heptane, octane, toluene, chlorobenzene, o-xylene, m-xylene, p-xylene, mecithylene, pentamethylbenzene, benzene, ethylbenzene, 1,3,5-triisopropylbenzene, o-dichlorobenzene, 1,2,4-trichlorobenzene and a mixture thereof.

It is preferable that the esterification reaction according to the present invention is carried out under a dry inert gas atmosphere, for example, under an argon or nitrogen atmosphere. The argon atmosphere may be generated by using a method where argon is allowed to slowly flow, and dehydration and deoxygenation atmospheres may be simultaneously accomplished by performing the reaction under the argon atmosphere.

In addition, in the condensation reaction of the monovalent carboxylic acid and monovalent alcohol or the polycondensation reaction of aliphatic polyvalent carboxylic acid and aliphatic polyvalent alcohol, it is preferable that the reaction is carried out under hot reflux at 100 to 250° C. for 24 to 72 hours. It is more preferable that the reaction is carried out at 120 to 180° C. for 1 to 24 hours.

Meanwhile, in the condensation reaction of the aromatic carboxylic acid and the aromatic alcohol, it is preferable that the reaction is carried out under hot reflux at 120 to 250° C. It is more preferable that the reaction is carried out at 150 to 200° C. for 24 to 72 hours.

In the present invention, since the ester compound that is obtained by the above esterification reaction condition does not generate side reactions by using the carboxylic acid and alcohol in almost the same mole number, it is not necessary to perform the purification, thus it is economical and convenient.

After the reaction of ester is finished, in order to repeatedly use the used catalyst, the following treatment may be carried out. The ionic liquid is added to the reaction system, the zirconium compound that is included in the esterification catalyst composition according to the present invention is extracted with the ionic liquid layer by using the ionic liquid, and the ester compound may be obtained from the organic layer. Here, the ionic liquid means a salt that has a property where the salt becomes liquid at room temperature or at a temperature that is close to room temperature. Since it has very high polarity and well dissolves metal salts, it may be suitably used to extract the catalyst used in the production method of the ester compound according to the present invention. The ionic liquid extracting the catalyst is washed with another organic solvent according to the necessity, and may be repeatedly used as a catalyst solution of the esterification reaction while the solvent is not removed under reduced pressure.

The ionic liquid that is used in the production method of the ester compound according to the present invention is not limited, but preferably 1-butyl-3-methylimidasoliumtrifluoromethansulfonimide, 1-ethyl-3-methylimidasoliumtrifluoromethansulfonate, N-alkylpyrydiniumtrifluoromethansulfonateimide, and more preferably N-butylpyrydiniumtrifluoromethansulfonateimide. The use amount of the ionic liquid is in the range of preferably 5 to 20 ml and more preferably 10 to 15 ml on the basis of 0.5 mmol of the total use amount of the catalyst.

Mode for Invention

Hereinafter, the present invention will be described in detail in light of Examples and Experimental Examples. The present invention may, however, be embodied in many different forms and should not be construed as being limited to the Examples and Experimental Examples set forth herein. Rather, these Examples and Experimental Examples are provided such that this disclosure will be thorough and complete and will fully convey the concept of the present invention to those skilled in the art.

In the following Examples, all operations that treated compounds sensible to air or water were performed by using a standard Schienk technique or a dry box technique. The nuclear magnetic resonance spectrum was performed by using a Bruker 300 spectrometer. The solvent such as xylene, toluene and the like was used while being not particularly purified. In addition, the esterification catalyst used in the following Examples was obtained from Strem Chemicals, Inc. in the USA, and used while being not subjected to additional processing.

Production of the Ester Compound

EXAMPLE 1

Esterifaction Reaction of 5-norbornene-2-methanol and the Cinnamic Acid—Use of the Zirconium Acetyl Acetonate Catalyst 5-norbornene-2-methanol (3.72 g, 30 mmol), the cinnamic acid (4.15 g, 32.4 mmol), and 30 ml of xylene were continuously added to the 250 ml flask. Zirconium acetyl acetonate [$Zr(acac)_4$] (1.46 g, 3 mmol, 10 mol %) was added thereto, and azeotropic reflux was performed. The temperature of the heated bath was controlled to 180° C. and the reaction was performed for 18 hours. After that, the reaction was finished after the GC check, and it was cooled to normal temperature. Thereafter, 30 ml of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.$NaHCO_3$ solution was added thereto and washed. This process was performed twice, and $MgSO_4$ was added to the separated organic solution to remove a small amount of water. After this was filtered by using $MgSO_4$, the solvent was removed under reduced pressure, and the purification process was carried out to obtain 7.09 g of cinnamic norbornene methyl ester (NB-Cin-H compound) that was the light yellow liquid compound (molecular weight=254.13, yield 93%).

EXAMPLE 2

Reaction of 5-norbornene-2-methanol and the cinnamic acid—Use of the tetrakis(2,2,6,6-tetramethyl-3,5-heptanedionato)zirconium catalyst 5-norbornene-2-methanol (1.86 g, 15 mmol), the cinnamic acid (1.98 g, 15.5 mmol), and 25 ml of xylene were continuously added to the 250 ml flask. Tetrakis(2,2,6,6-tetramethyl-3,5-heptanedionato)zirconium [$Zr(TMHD)_4$] (1.24 g, 1.5 mmol, 10 mol %) was added thereto, and azeotropic reflux was performed. The temperature of the heated bath was controlled to 180° C. and the reaction was performed for 18 hours. After that, the reaction was finished after the GC check, and it was cooled to normal temperature. Thereafter, 30 ml of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.$NaHCO_3$ solution was added thereto and washed. This process was performed twice, and $MgSO_4$ was added to the separated organic solution to remove a small amount of water. After water was removed, this was filtered by using $MgSO_4$, and the solvent was removed under reduced pressure. The purification process was carried out to obtain 3.38 g of cinnamic norbornene methyl ester (NB-Cin-H compound) that was the light yellow liquid compound (molecular weight=254.13, yield 88.7%).

EXAMPLE 3

Reaction of 5-norbornene-2-methanol and the cinnamic acid—Use of the zirconium hexafluoroacetyl acetonate catalyst 5-norbornene-2-methanol (1.86 g, 15 mmol), the cinnamic acid (1.98 g, 15.5 mmol), and 25 ml of xylene were continuously added to the 250 id flask. Zirconium hexafluoroacetylacetonate $Zr(CF_3COCHCOCF_3)_4$ (1.38 g, 1.5 mmol, 10 mol %) was added thereto, and azeotropic reflux was performed. The temperature of the heated bath was controlled to 180° C. and the reaction was performed for 18 hours. After that, the reaction was finished after the GC check, and it was cooled to normal temperature. Thereafter, 30 ml of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.$NaHCO_3$ solution was added thereto and washed. This process was performed twice, and $MgSO_4$ was added to the separated organic solution to remove a small amount of water. After water was removed, this was filtered by using $MgSO_4$, and the solvent was removed under reduced pressure. The purification process was carried out to obtain 3.11 g of cinnamic norbornene methyl ester (NB-Cin-H compound) that was the light yellow liquid compound (molecular weight=254.13, yield 81.5%).

EXAMPLE 4

Reaction of 5-norbornene-2-methanol and the cinnamic acid—Use of the zirconium trifluoroacetyl acetonate catalyst 5-norbornene-2-methanol (1.86 g, 15 mmol), the cinnamic acid (1.98 g, 15.5 mmol), and 25 ml of xylene were continuously added to the 250 ml flask. Zirconium trifluoroacetyl acetonate $Zr(CF_3COCHCOCH_3)_4$ (1.06 g, 1.5 mmol, 10 mol %) was added thereto, and azeotropic reflux was performed. The temperature of the heated bath was controlled to 180° C. and the reaction was performed for 18 hours. After that, the reaction was finished after the GC check, and it was cooled to normal temperature. Thereafter, 30 ml of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.$NaHCO_3$ solution was added thereto and washed. This process was performed twice, and $MgSO_4$ was added to the separated organic solution to remove a small amount of water. After water was removed, this was filtered by using $MgSO_4$, and the solvent was removed under reduced pressure. The purification process was carried out to obtain 3.33 g of cinnamic norbornene methyl ester (NB-Cin-H compound) that was the light yellow liquid compound (molecular weight=254.13, yield 87.3%).

EXAMPLE 5

Reaction of Allyl Alcohol and the Cinnamic Acid—Use of the Zirconium Acetyl Acetonate Catalyst Allyl alcohol (1.74 g, 30 mmol), the cinnamic acid (4.15 g, 32.4 mmol), and 30 ml of xylene were continuously added to the 250 ml flask. Zirconium acetyl acetonate [Zr(acac)$_4$] (0.15 g, 0.3 mmol, 1 mol %) was added thereto, and azeotropic reflux was performed. The temperature of the heated bath was controlled to 180° C. and the reaction was performed for 18 hours. After that, the reaction was finished after the GC check, and it was cooled to normal temperature. Thereafter, 30 ml of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.NaHCO$_3$ solution was added thereto and washed. This process was performed twice, and MgSO$_4$ was added to the separated organic solution to remove a small amount of water. After water was removed, this was filtered by using MgSO$_4$, and the solvent was removed under reduced pressure. The purification process was carried out to obtain 5.34 g of cinnamic norbornene methyl ester (NB-Cin-H compound) that was the colorless liquid compound (molecular weight=189.24, yield 94%).

EXAMPLE 6

Reaction of benzyl alcohol and the 4-phenyl butyric acid—Use of the zirconium acetyl acetonate catalyst Benzyl alcohol (1.62 g, 15 mmol), 4-phenyl butyric acid (2.46 g, 15 mmol) and 25 ml of toluene were continuously added to the 250 ml flask. Zirconium acetyl acetonate [Zr(acac)$_4$] (0.731 g, 0.15 mmol, 1 mol %) was added thereto, and azeotropic reflux was performed. The temperature of the heated bath was controlled to 150° C. and the reaction was performed for 18 hours. After that, the reaction was finished after the GC check, and it was cooled to normal temperature. Thereafter, 30 ml of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.NaHCO$_3$ solution was added thereto and washed. This process was performed twice, and MgSO$_4$ was added to the separated organic solution to remove a small amount of water. After water was removed, this was filtered by using MgSO$_4$, and the solvent was removed under reduced pressure. The purification process was carried out to obtain 2.81 g of cinnamic norbornene methyl ester (NB-Cin-H compound) that was the colorless liquid compound (molecular weight=254.13, yield 99%).

EXAMPLE 7

Reaction of 5-norbornene-2-carboxylic acid

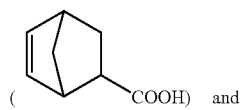

and

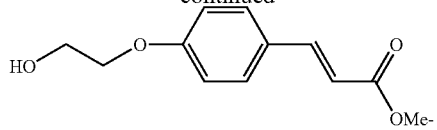

-continued

Use of the zirconium acetyl acetonate catalyst 5-norbornene-2-carboxylic acid (1.87 g, 15 mmol), alcohol (3.0 g, 13.5 mmol) that was represented by

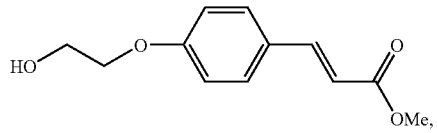

and 25 ml of toluene were continuously added to the 250 ml flask. Zirconium acetyl acetonate [Zr(acac)$_4$] (0.658 g, 0.135 mmol, 1 mol %) was added thereto, and azeotropic reflux was performed. The temperature of the heated bath was controlled to 150° C. and the reaction was performed for 18 hours. After that, the reaction was finished after the GC check, and it was cooled to normal temperature. Thereafter, 30 mlm of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.NaHCO$_3$ solution was added thereto and washed. This process was performed twice, and MgSO$_4$ was added to the separated organic solution to remove a small amount of water. After water was removed, this was filtered by using MgSO$_4$, and the solvent was removed under reduced pressure. The purification process was carried out to obtain 4.15 g of the compound (molecular weight=342.15, yield 89%).

COMPARATIVE EXAMPLE 1

Esterification reaction of 5-norbornene-2-methanol and the cinnamic acid—Use of amberlist 15 catalyst 5-norbornene-2-methanol (3.72 g, 30 mmol), the cinnamic acid (4.15 g, 32.4 mmol), and 30 ml of xylene were continuously added to the 250 ml flask. Amberlist 15 (the heterogenous catalyst form where the sulfonic acid substituent group was provided on polystyrene, 0.37 g, 10 wt %) was added thereto, and azeotropic reflux was performed. The temperature of the heated bath was controlled to 180° C. and the reaction was performed for 18 hours. After that, the reaction was finished after the GC check, and it was cooled to normal temperature. Thereafter, 30 ml of ethyl acetic acid was added thereto. After the undissolved solid compound is precipitated, 30 ml of 1 M (mol/L) dilute hydrochloric acid solution was added thereto, and the washing was performed. This process was performed twice, and 30 ml of the saturated aq.NaHCO$_3$ solution was added thereto and washed. This process was performed twice, and MgSO$_4$ was added to the separated organic solution to remove a small amount of water. This was filtered by using MgSO$_4$, and the solvent was removed under reduced pressure. The purification process was carried out to obtain 3.28 g of cinnamic norbornene methyl ester (NB-Cin-H compound) that was the light yellow liquid compound (molecular weight=254.13, yield 43%).

The invention claimed is:
1. A method for producing an ester compound, the method comprising the steps of:
esterifying alcohol and carboxylic acid compounds by using the esterification catalyst composition comprising a compound that is represented by the following Formula I:

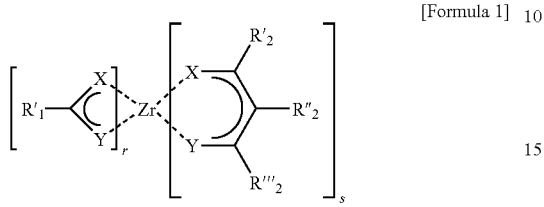

[Formula 1]

wherein X and Y are each independently a hetero atom that is S or O;
$R_1'$, $R_2'$, $R_2''$ and $R_2'''$ are each independently any one selected from the group consisting of hydrogen; halogen; straight- or branched-chained alkyl having 1 to 20 carbon atoms, haloalkyl, vinylalkoxy, haloalkoxy, carbonyloxy, halocarbonyloxy; straight- or branched-chained alkenyl that is unsubstituted or substituted with hydrocarbons and has 1 to 20 carbon atoms; cycloalkyl that is unsubstituted or substituted with hydrocarbons and has 3 to 12 carbon atoms; aryl that is unsubstituted or substituted with hydrocarbons and has 6 to 40 carbon atoms; aralkyl that is unsubstituted or substituted with hydrocarbons and has 7 to 15 carbon atoms; alkynyl having 2 to 20 carbon atoms; alkynyl having 2 to 20 carbon atoms; straight- or branched-chained alkoxy that is unsubstituted or substituted with halogen, vinyl or hydrocarbons and has 1 to 20 carbon atoms; straight- or branched-chained carbonyloxy that is unsubstituted or substituted with halogen, or hydrocarbons and has 1 to 20 carbon atoms,
r and s are each independently an integer in the range of 0 to 4, and r+s=4, and
the hydrocarbons may be selected from the group consisting of a methyl group, an ethyl group, a propyl group, an isopropyl group, a butyl group, a tertiary-butyl group, a pentyl group, a hexyl group, a heptyl group, a cyclopentyl group a cyclohexyl group, a phenyl group, a naphthyl group, an anthracenyl group, a biphenyl group, a pyrenyl group, and a perylenyl group
wherein the alcohol includes compounds that are represented by the following Formula 3:

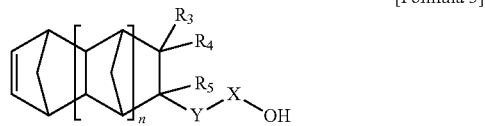

[Formula 3]

wherein n is an integer in the range of 0 to 4,
Y is a direct bond; or a polar functional group selected from the group consisting of —C(O)—O—, —O—C(O)—, —C(O)N($R_3$)—, —OC(O)N($R_3$)—, —N($R_3$)—, —C(O)—, —$SO_2$—, $SO_3$— and —$OSO_2$—,
X is a direct bond; or any one selected from the group consisting of —(OCH$_2$)$_m$— (m is an integer in the range of 0 to 10); substituted or unsubstituted alkylene having 1 to 20 carbon atoms; substituted or unsubstituted alkenylene having 2 to 20 carbon atoms; substituted or unsubstituted cycloalkylene having 3 to 12 carbon atoms; substituted or unsubstituted arylene having 6 to 40 carbon atoms; substituted or unsubstituted aralkylene having 7 to 15 carbon atoms; and substituted or unsubstituted alkynylene having 2 to 20 carbon atoms;
$R_3$, $R_4$ and $R_5$ are each independently any one selected from the group consisting of hydrogen; halogen; straight- or branched-chained alkyl having 1 to 20 carbon atoms; straight- or branched-chained vinyl or alkenyl having 2 to 20 carbon atoms; alkynyl having 2 to 20 carbon atoms; cycloalkyl that is unsubstituted or substituted with hydrocarbons and has 3 to 12 carbon atoms; aryl that is unsubstituted or substituted with hydrocarbons and has 6 to 40 carbon atoms; and aralkyl that is unsubstituted or substituted with hydrocarbons and has 7 to 15 carbon atoms,
wherein the carboxylic acid includes compounds that are represented by the following Formulas 11 to 14:

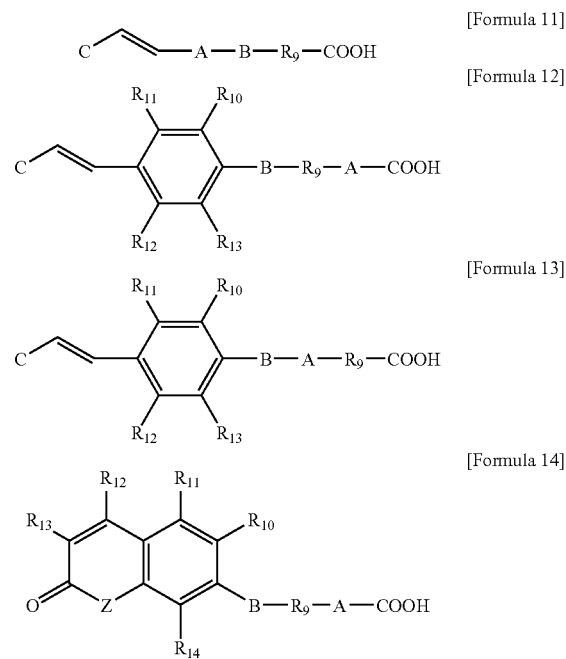

[Formula 11]
[Formula 12]
[Formula 13]
[Formula 14]

wherein
A is a direct bond; or any one selected from the group consisting of substituted or unsubstituted alkylene having 1 to 20 carbon atoms; carbonyl [—C(O)—]; carboxy [—C(O)O— or —OC(O)—]; and substituted or unsubstituted arylene having 6 to 40 carbon atoms,
B is a direct bond; oxygen, sulfur or —NH—,
Z is oxygen or sulfur,
$R_9$ is a direct bond; or any one selected from the group consisting of substituted or unsubstituted alkylene having 1 to 20 carbon atoms; substituted or unsubstituted alkenylene having 2 to 20 carbon atoms; substituted or unsubstituted cycloalkylene having 3 to 12 carbon atoms; substituted or unsubstituted arylene having 6 to 40 carbon atoms; substituted or unsubstituted aralkylene having 7 to 15 carbon atoms; and substituted or unsubstituted alkynylene having 2 to 20 carbon atoms,
$R_{10}$, $R_{11}$, $R_{12}$, $R_{13}$ and $R_{14}$ are each independently any one selected from the group consisting of substituted or unsubstituted alkyl having 1 to 20 carbon atoms; substituted or unsubstituted alkoxy having 1 to 20 carbon atoms; substituted or unsubstituted aryloxy having 6 to 30 carbon atoms; and substituted or unsubstituted aryl having 6 to 40 carbon atoms, and C is a compound that includes hetero aryl including Groups 14, 15, or 16 heteroatoms and having 6 to 40 carbon atoms; or aryl having 6 to 40 carbon atoms.

2. The method for producing an ester compound as set forth in claim 1, wherein the esterification catalyst composition is used at a ratio of 0.01 to 20 on the basis of a mole number of the compound that is added in a smaller amount among the alcohol and carboxylic acid compounds.

3. The method for producing an ester compound as set forth in claim 1, wherein in the esterification catalyst composition, a solvent is added at a ratio of 0.1 to 100 on the basis of a mole number of the compound that is added in a smaller amount among the alcohol and carboxylic acid compounds.

* * * * *